United States Patent
Kim

[11] Patent Number: 6,159,226
[45] Date of Patent: Dec. 12, 2000

[54] TONGUE CLEANING DEVICE

[76] Inventor: Han-Joon Kim, c/o KIM Orthodontic Clinic, Pain-Kurakuen 2F, 3-3, Ishibane-cho, Nishinomiya-shi, Hyogo-ken 662-0074, Japan

[21] Appl. No.: 09/309,600

[22] Filed: May 11, 1999

[30] Foreign Application Priority Data

May 12, 1998 [JP] Japan .................................. 10-129194

[51] Int. Cl.$^7$ .................................................. A61B 17/24
[52] U.S. Cl. ............................................................ 606/161
[58] Field of Search ..................................... 606/161, 162

[56] References Cited

U.S. PATENT DOCUMENTS

| | | |
|---|---|---|
| 1,983,601 | 12/1934 | Conn . |
| 4,538,631 | 9/1985 | Prince . |
| 4,672,953 | 6/1987 | DiVito . |
| 5,779,654 | 7/1998 | Foley et al. ............................. 606/161 |

FOREIGN PATENT DOCUMENTS

| | | |
|---|---|---|
| 468322 | 7/1914 | France . |
| 29 618 012 | 2/1997 | Germany . |

*Primary Examiner*—Michael Buiz
*Assistant Examiner*—Vy Q. Bui
*Attorney, Agent, or Firm*—Rabin & Champagne, PC

[57] ABSTRACT

A tongue cleaning device has not been available which ensures easy and satisfactory tongue cleaning for prevention of halitosis. To solve the problem, a tongue cleaning device is provided which is adapted to suck a tongue surface through a cylindrical member 11 by a suction system while scraping the tongue surface with spatulate members 14 and brushes 15. Papillae on the tongue surface are successively raised or laid down by scraping the tongue surface with the spatulate members 14 and brushes 15. Therefore, fossae of the tongue papillae and fissurae and sulci between the tongue papillae are spread so that bacterial plaque and bacteria can be sucked out of the sulci and the like by the suction system. Thus, the tongue can easily be cleaned.

33 Claims, 5 Drawing Sheets

TONGUE CLEANING DEVICE

This application is based on an application No. 10-129194 filed in Japan, the content of which is incorporated hereinto by reference.

BACKGROUND OF THE INVENTION

1. Field of the Invention

The present invention relates to a tongue cleaning device for cleaning a tongue.

2. Description of the Prior Art

In recent years, a treatment for prevention of halitosis has widely been performed in Western countries. The halitosis is supposedly caused by periodontal diseases, a furry tongue, oral dryness, stresses, and irritative food and drink. A tongue cleaning treatment receives attention as one of the most effective methods for the prevention of the halitosis.

Bacterial plaque which produces volatile sulfur compounds is responsible for the halitosis deposits in fossae of papillae on the surface of the tongue. The bacterial plaque and bacteria present therein cause not only the halitosis but also hypoorexia, hypogeusia, dental caries and stomatitis. Therefore, the tongue cleaning is important for oral hygiene and health care.

One common method for the tongue cleaning is to use a tooth brush. However, it is difficult to sufficiently remove the bacterial plaque and bacteria present in fissurae and sulci between the papillae of the tongue by the brush tongue cleaning method.

Various tongue cleaning tools such as thin edged spatulate plastic and metal tools (generally called "tongue cleaners") have been devised and are commercially available.

Such a tongue cleaner, if not properly used, will fail to sufficiently remove the bacterial plaque and bacteria present in the fissurae and sulci of the tongue. In addition, improper use of the tongue cleaner may result in damage to the tongue surface.

Oral hygienic practitioners, such as dentists, desire need to device to remove, in a reliable and professional manner, the bacterial plaque from the tongue of a patient who cannot properly perform the tongue cleaning, such as old or handicapped person who need nursing and have difficulty in performing the tongue cleaning.

SUMMARY OF THE INVENTION

In view of the foregoing, it is an object of the present invention to provide a tongue cleaning device which ensures easy and satisfactory tongue cleaning.

It is another object of the present invention to provide a tongue cleaning device (tongue cleaning vacuum tip) which is used for the tongue cleaning in a dental clinic or the like equipped with a dental treatment unit and is attachable to a suction system of the dental treatment unit.

In accordance with a first embodiment of the present invention, there is provided a tongue cleaning device comprising: a flexible tube; a suction system connected to a proximal end of the tube; a handle provided adjacent a distal end of the tube; a cylindrical member connected to the distal end of the tube; and a scraping member attached to a tip portion of the cylindrical member for scraping a tongue surface, whereby the tongue surface being scraped with the scraping member is sucked through the cylindrical member by the suction system.

In accordance with a further inventive aspect of the invention, a tongue cleaning device is characterized in that the cylindrical member is detachable.

In accordance with a further inventive aspect of the invention, wherein the scraping member includes a spatulate member.

In accordance with a further inventive aspect of the invention, the scraping member includes a brush or brushy projections.

In accordance with a further inventive aspect of the invention, is characterized in that the scraping member is disposed transversely of a tip opening of the cylindrical member.

In accordance with a second embodiment of the invention, there is provided a tongue cleaning device comprising: a suction system; a cylindrical member having a proximal end connected to the suction system; and a scraping member attached to a distal end of the cylindrical member for scraping a tongue surface, whereby the tongue surface being scraped with the scraping member is sucked through the cylindrical member by the suction system.

In accordance with an inventive aspect of the second embodiment, is characterized in that the cylindrical member is detachable.

In accordance with an inventive aspect of the second embodiment, is characterized in that the scraping member includes a spatulate member.

In accordance with an inventive aspect of the second embodiment, is characterized in that the scraping member includes a brush or brushy projections.

In accordance with an inventive aspect of the second embodiment, is characterized in that the scraping member is disposed transversely of a tip opening of the cylindrical member.

In accordance with an inventive aspect of the second embodiment claim 11, there is provided a cylindrical member for a tongue cleaning device comprising a scraping member provided at a distal end of the cylindrical member for scraping a tongue surface, whereby the tongue surface being scraped with the scraping member is sucked through the cylindrical member by a suction system.

In accordance with an inventive aspect of the second embodiment, is characterized in that the scraping member includes a spatulate member.

In accordance with an inventive aspect of the second embodiment, is characterized in that the scraping member includes a brush or brushy projections.

In accordance with an inventive aspect of the second embodiment, is characterized in that the scraping member is disposed transversely of a tip opening of the cylindrical member.

With the aforesaid features, the tongue surface is scraped with the scraping member while being sucked by the suction system. Therefore, the tongue can satisfactorily be cleaned. Since papillae on the tongue surface are successively raised or laid down by softly scraping the tongue surface with the scraping member, fossae of the tongue papillae and fissurae and sulci between the tongue papillae are spread so that bacterial plaque and bacteria can be sucked out of the sulci and the like by the suction system.

Where the scraping member is comprised of the spatulate member, the scraping member ensures satisfactory cleaning of the tongue surface like the conventional tongue cleaner.

Where the scraping member is comprised of the brush or brushy projections, bristles of the brush or the brushy projections enter the fossae of the tongue papillae and, in conjunction with the suction, ensure satisfactory tongue cleaning.

Where the scraping member is disposed transversely of the tip opening of the cylindrical member, a portion of the tongue being scraped with the scraping member can satisfactorily be sucked.

Where the cylindrical member is detachable, family members, for example, can use their own cylindrical members for the tongue cleaning by changing the cylindrical member. This is good in hygienic sense. Further, the scraping member can readily be replaced if it becomes dirty.

In accordance with the present invention, a tongue cleaning device is provided which ensures satisfactory tongue cleaning.

DESCRIPTION OF THE PREFERRRED EMBODIMENTS

Figure 1:
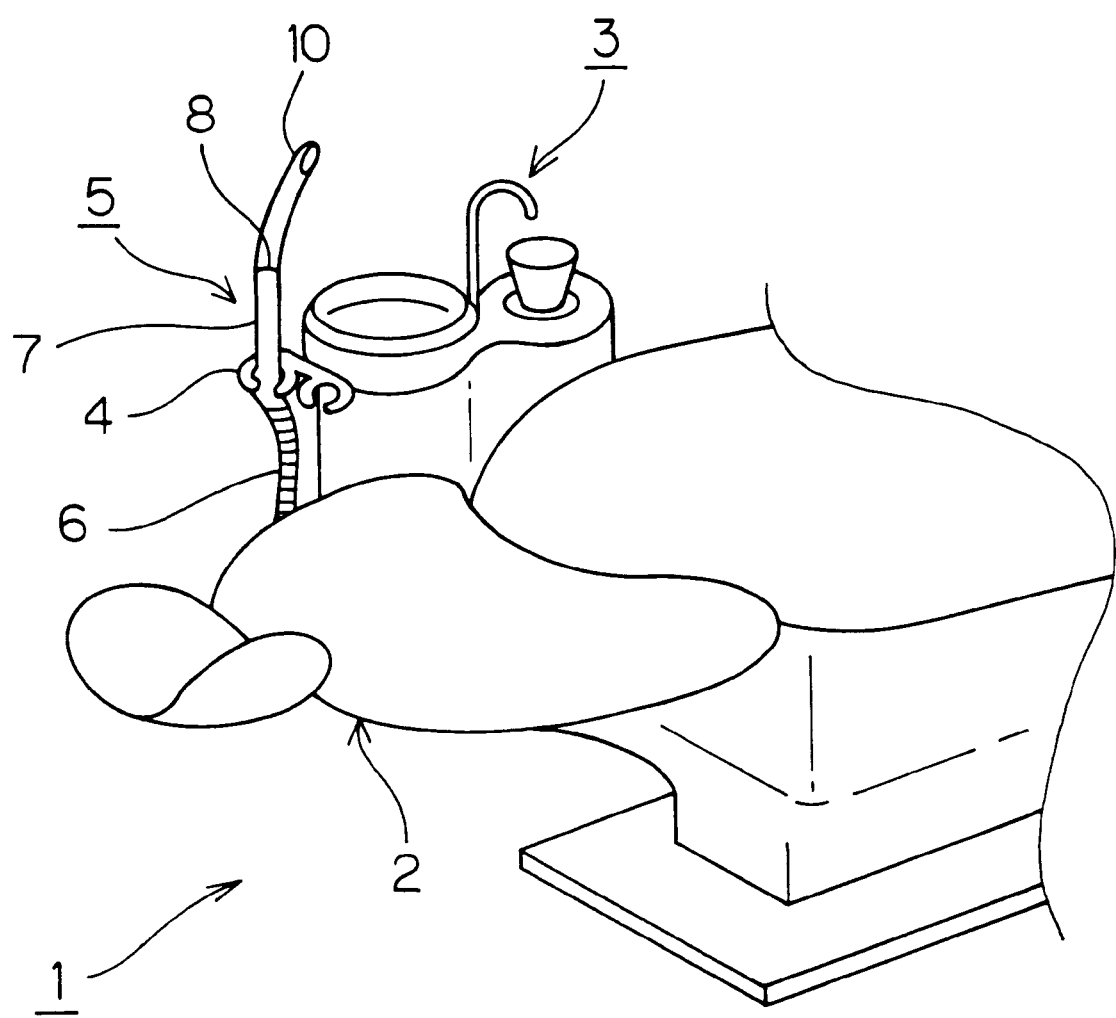
FIG. 1 is a diagram illustrating a portion of a dental treatment unit equipped-with a tongue cleaning device according to one embodiment of the present invention.

FIG. 1 is a perspective view illustrating a portion of a dental chair unit equipped with a tongue cleaning device according to one embodiment of the present invention. The chair unit 1 includes a chair 2 having a reclinable chair back and head rest. A mouth rinsing unit 3 is provided on a lateral side of the chair 2. A holder 4 is provided in association with the mouth rinsing unit 3, and a tip portion of a vacuum cleaner 5 is held by the holder 4.

The vacuum cleaner 5 includes a silicone tube 6 having a proximal end connected to a vacuum suction system not shown, a handle 7 provided adjacent a distal end of the silicone tube 6, and a suction port 8 formed in a tip portion of the handle 7. The vacuum cleaner 5 is mainly used for evacuating saliva accumulated in an oral cavity of a patient during dental treatment with a vacuum nozzle attached to the suction port 8.

A tongue cleaning vacuum tip 10 which is one example of the tongue cleaning device according to this embodiment is attached to the suction port 8 at the tip of the vacuum cleaner 5 for use.

Figure 2:
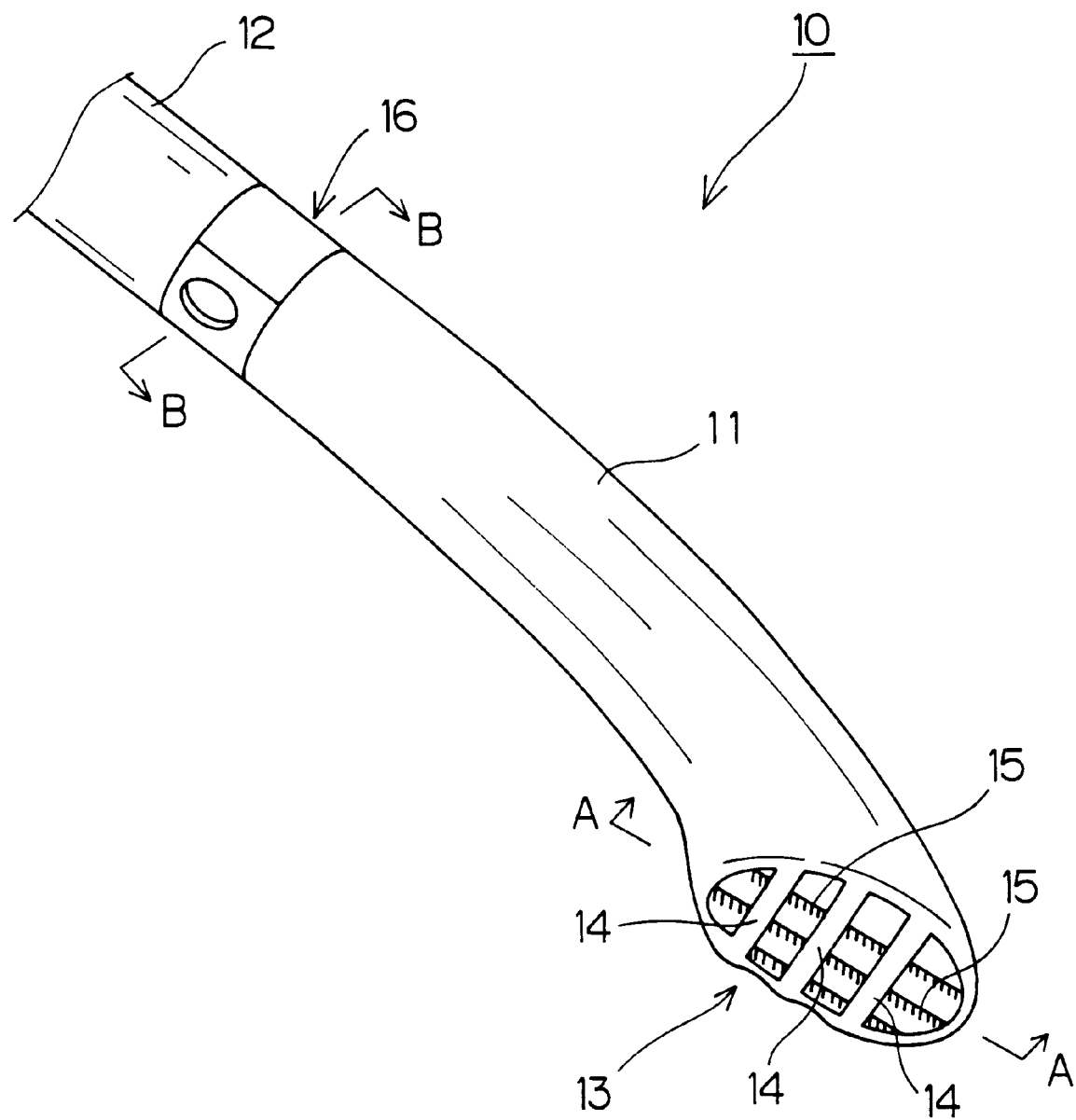
FIG. 2 is a perspective view illustrating a tongue cleaning vacuum tip according to the embodiment of the present invention.

FIG. 2 is a perspective view illustrating one exemplary construction of the tongue cleaning vacuum tip 10. The vacuum tip 10 includes a cylindrical member 11, formed of a resin, which has a rear end to be connected to the suction port 8 of the vacuum cleaner 5 as described above. More specifically, the outer diameter of the rear end 12 of the cylindrical member 11 is slightly smaller than the inner diameter of the suction port 8, so that the rear end 12 can be inserted into the suction port 8. The construction of the rear end 12 of the cylindrical member 11 is not limited to that described above. However, it is preferable if the rear end 12 is configured so as to be connected to the suction port 8 at the tip of the vacuum cleaner 5. For example, the rear end 12 of the cylindrical member 11 may be threaded for thread engagement with the suction port.

In this embodiment, the vacuum tip 10 is disposable, which is replaced for each patient. Alternatively, the cylindrical member 11 may be made of a metal or the like so that the vacuum tip 10 can repeatedly be used after cleaning thereof.

The cylindrical member 11 has an opening 13 formed angularly with respect to the length thereof at its distal end. Spatulate members 14 and brushes (or brushy projections) 15 are provided across the opening 13.

Figure 3:
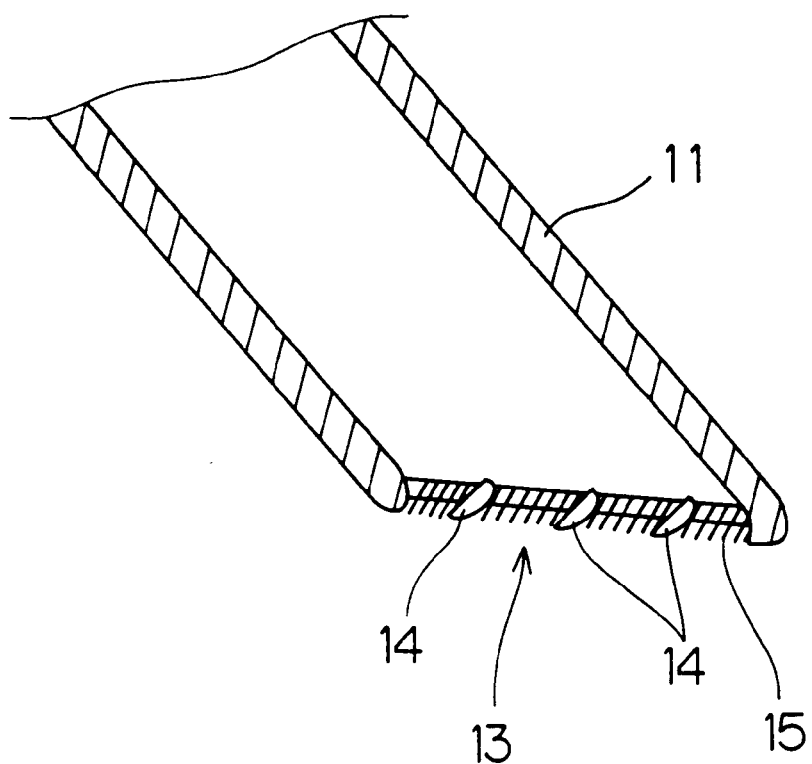
FIG. 3 is a sectional view taken along a line A—A in FIG. 2.

FIG. 3 is a sectional view of the tip portion of the vacuum tip 10 taken along a line A—A in FIG. 2. Referring to FIGS. 2 and 3, spatulate members 14 are provided transversely of the opening 13 as extending perpendicularly to the length of the cylindrical member 11. As shown in FIG. 3, the spatulate members are tilted, so that edges of the spatulate members 14 are oriented rearwardly of the cylindrical member 11. When the tongue surface is to be scraped with the vacuum tip 10, the vacuum tip 10 is dragged rearward. The aforesaid construction ensures that the tongue surface can effectively be scraped with the edges of the spatulate members 14 during the dragging movement of the vacuum tip 10.

In this embodiment, the spatulate members 14 are formed of a resin integrally with the cylindrical member 11 as shown in FIG. 2. The edges of the spatulate members 14 are undulatory to ensure effective scraping of the tongue surface. The spatulate members 14 are not necessarily required to have such a configuration, but may each have a straight edge.

The brushes 15 are disposed longitudinally of the opening 13 and substantially perpendicularly to the spatulate members 14. It is noted that the brushes 15 are not necessarily provided perpendicularly to the spatulate members 14, but may be provided parallel to the spatulate members 14. It is preferred that the spatulate members 14 and the brushes 15 be configured and arranged so that the tongue surface can effectively be scraped with the spatulate members 14 and the brushes 15, i.e., the papillae on the tongue surface can successively be raised or laid down by the spatulate members 14 and the brushes 15 for exposure of spaces between the papillae. Since the tongue surface can be sucked by the suction system with the spaces between the papillae being exposed, the bacterial plaque and bacteria present therein can be removed.

Figure 4:
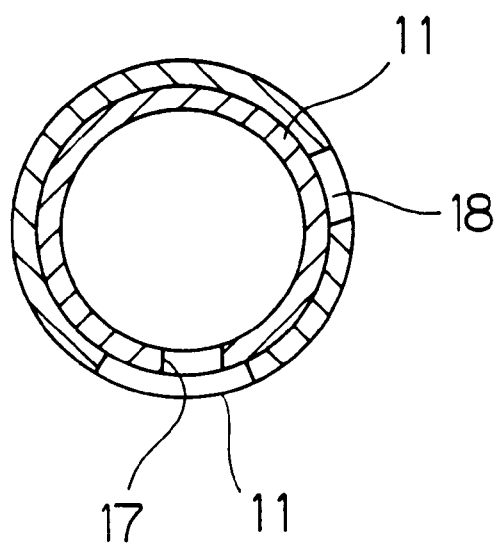
FIG. 4 is a sectional view taken along a line B—B in FIG. 2.

The cylindrical member 11 may include a suction force controlling mechanism 16. FIG. 4 is a sectional view taken along a line B—B in FIG. 2. Referring to FIGS. 2 and 4, the suction force controlling mechanism 16 has a small hole 17 formed in the cylindrical member 11, and a C-shaped ring 18 for exposing and covering the small hole 17. The ring 18 is rotated to expose the small hole 17, whereby air is sucked from the small hole 17. Thus, the suction force at the tip opening 13 of the cylindrical member 11 can be reduced. On the other hand, the suction force at the tip opening 13 can be increased by covering the small hole 17 with the ring 18.

The construction of the suction force controlling mechanism 16 is not limited to that described above, but the mechanism 16 may have any other construction.

FIG. 5 illustrates another exemplary construction of the scraping member to be provided at the tip of the cylindrical member 11.

Figure 5A:
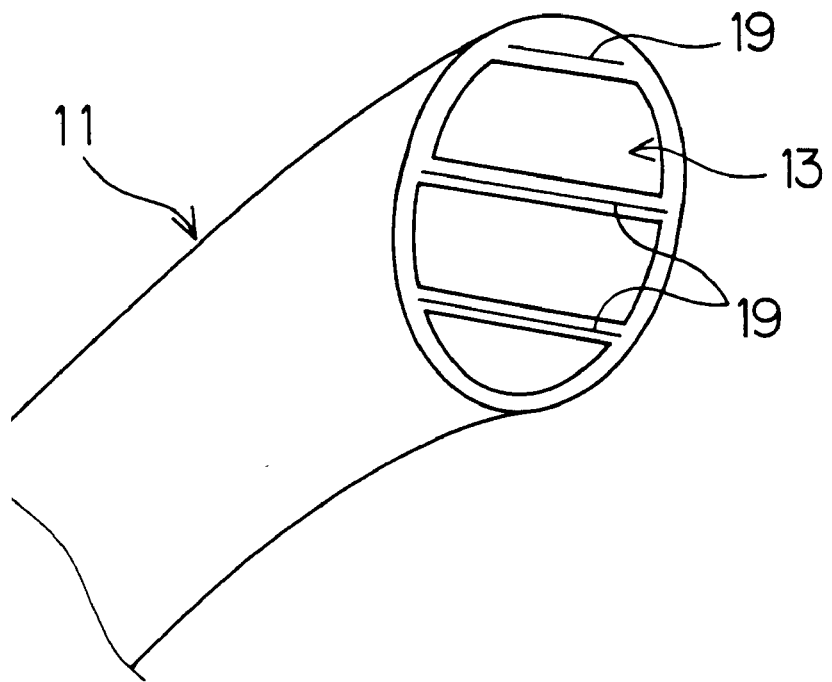
FIG. 5 is a diagram illustrating another exemplary construction of the scraping member.

As shown in FIG. 5A, the scraping member may be comprised of a plurality of spatulate members 19 provided transversely of the tip opening 13 of the cylindrical body 11.

Although a scraping member comprised of three spatulate members extending parallel to each other is shown in FIG. 5A, the spatulate members 19 may be arranged in a grid pattern.

Figure 5B:
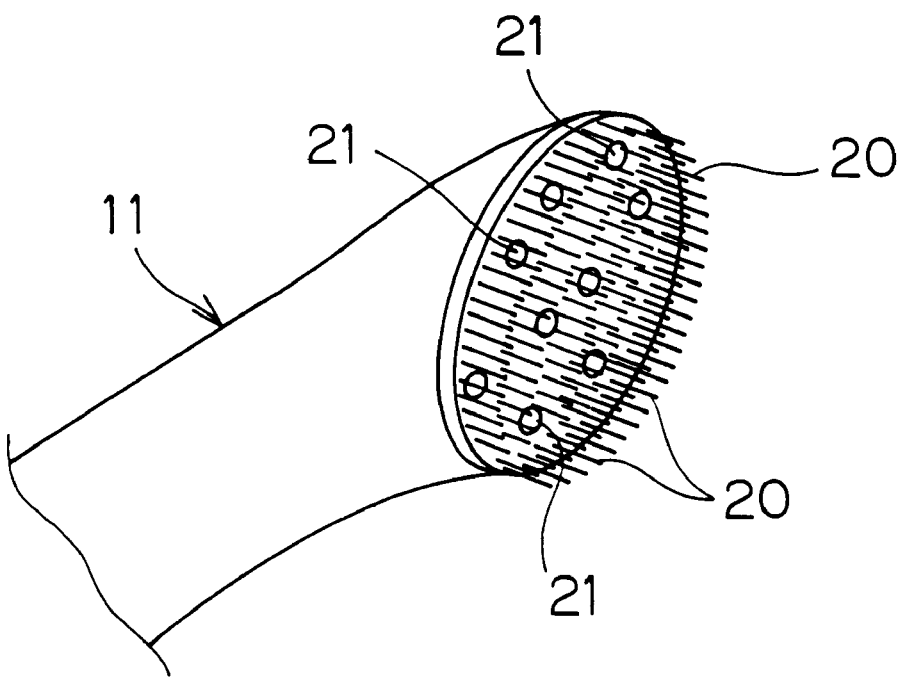

As shown in FIG. 5B, the scraping member may be constructed such that short bristles for a brush 20 are implanted on the tip portion of the cylindrical member 11 with no tip opening formed in the tip portion and a plurality of small holes 21 are formed in the tip portion of the cylindrical member in the vicinity of a lower portion of the brush 20. Brushy projections may be provided instead of the brush 20.

Figure 6:
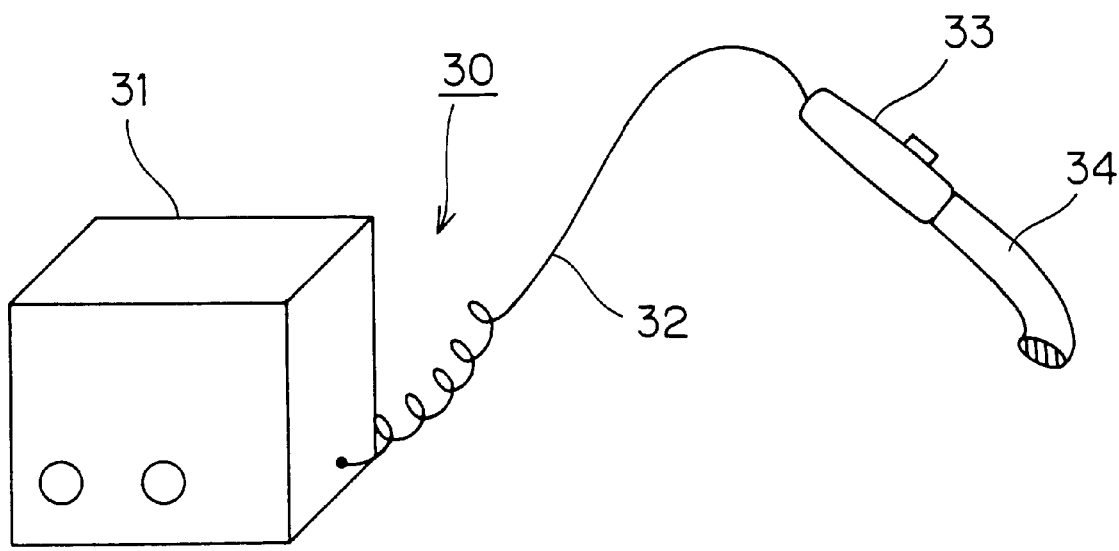
FIG. 6 is a schematic diagram illustrating a tongue cleaning device for domestic use according to another embodiment of the present invention.

FIG. 6 is a schematic diagram illustrating a tongue cleaning device according to another embodiment of the present invention. While the aforesaid embodiment is applicable to a dental treatment unit and the like, the tongue cleaning device shown in FIG. 6 is for domestic use.

Referring to FIG. 6, the tongue cleaning device 30 includes a main body 31, a tube 32 extending from the main body 31, a handle 33 provided adjacent a distal end of the tube 32, and a tip 34 detachably attached to a tip portion of the handle 33. A suction system (such as comprising a motor and a pump) not shown is incorporated in the main body 31. The suction system is connected to a proximal end of the tube 32. The tube 32 is flexible so that an operator can freely operate the tip 34 attached to the tip portion of the handle in an oral cavity of a patient by holding the handle 33.

The tip 34 has substantially the same construction as the tongue cleaning vacuum tip 10 according to the embodiment described above. More specifically, the tip 34 is a cylindrical member having an opening formed at its tip portion and a scraping member (e.g., spatulate members, brushes and brushy projections) provided at the opening.

The tip 34 is detachable from the handle 33. Therefore, when the tongue cleaning device 30 is shared among family members, the tip 34 can be replaced for each of the family members. This is good in hygienic sense. Further, the tip 34 can readily be replaced if the tip 34 becomes dirty.

Although the main body 31 and the handle 33 are connected to each other-through the tube 32 in accordance with the embodiment shown in FIG. 6, the construction of the tongue cleaning device is not limited thereto. For example, the suction system may be integral with the handle 33 as in the case of a portable electric tooth brush, so that a user can hold the entire device for use.

It should be noted-that-the present invention is not limited to the embodiments described above and various changes may be made within the scope of the present invention defined by the claims.

What is claimed is:

1. A tongue cleaning device, comprising:
   a flexible tube;
   a suction system connected to a proximal end of the flexible tube;
   a handle provided adjacent a distal end of the flexible tube;
   a cylindrical member connected to the distal end of the flexible tube; and
   a scraping member attached to a tip portion of the cylindrical member for scraping a tongue surface, said scraping member including at least one spatulate member that extends across an opening of said cylindrical member, and being tilted relative to the opening so that one longitudinal edge of said spatulate member is disposed closer to a rear edge of the opening than another longitudinal edge of said spatulate member, whereby debris on the tongue surface being scraped with the scraping member is sucked through the cylindrical member by the suction system.

2. A tongue cleaning device as set forth in claim 1, wherein the cylindrical member is detachable.

3. A tongue cleaning device as set forth in claim 2, wherein the scraping member includes a brush or brushy projections.

4. A tongue cleaning device as set forth in claim 2, wherein the scraping member is disposed transversely of the opening of the cylindrical member.

5. A tongue cleaning device as set forth in claim 1, wherein said cylindrical member extends in a longitudinal direction; and wherein the opening is arranged at an angle relative to the longitudinal direction, so that the opening has a length and a width, with the length being greater than the width.

6. A tongue cleaning device as set forth in claim 5, wherein said at least one spatulate member extends across the width of the opening.

7. A tongue cleaning device as set forth in claim 6, wherein said at least one spatulate member comprises a plurality of spatulate members, each extending across the width of the opening.

8. A tongue cleaning device as set forth in claim 5, wherein said scraping member further includes a brush that extends across the opening.

9. A tongue cleaning device as set forth in claim 8, wherein said brush extends transversely to said spatulate member.

10. A tongue cleaning device as set forth in claim 8, wherein said brush and said spatulate member are arranged at essentially the same level.

11. A tongue cleaning device as set forth in claim 1, wherein said spatulate member has a undulating edge.

12. A tongue cleaning device as set forth in claim 1, wherein said cylindrical member includes a hole formed in a side wall thereof, and a C-shaped ring selectively movable over the hole to open or close the hole, whereby when the hole is open, said suction system applies a minimum suction to the opening, and when the hole is closed, said suction system applies a maximum suction to the opening.

13. A tongue cleaning device as set forth in claim 1, wherein said at least one spatulate member comprises a plurality of spatulate members arranged in a grid pattern.

14. A tongue cleaning device, comprising:
   a suction system;
   a cylindrical member having a proximal end connected to the suction system; and
   a scraping member attached to a distal end of the cylindrical member for scraping a tongue surface, said scraping member including at least one spatulate member that extends across an opening of said cylindrical member, and being tilted relative to the opening so that one longitudinal edge of said spatulate member is disposed closer to a rear edge of the opening than another longitudinal edge of said spatulate member, whereby debris on the tongue surface being scraped with the scraping member is sucked through the cylindrical member by the suction system.

15. A tongue cleaning device as set forth in claim 14, wherein the cylindrical member is detachable.

16. A tongue cleaning device as set forth in claim 14, wherein the scraping member includes a brush or brushy projections.

17. A tongue cleaning device as set forth in claim 14, wherein the scraping member is disposed transversely of the opening of the cylindrical member.

18. A tongue cleaning device as set forth in claim 14, wherein said cylindrical member extends in a longitudinal direction; and wherein the opening is arranged at an angle relative to the longitudinal direction, so that the opening has a length and a width, with the length being greater than the width.

19. A tongue cleaning device as set forth in claim 18, wherein said at least one spatulate member extends across the width of the opening.

20. A tongue cleaning device as set forth in claim 19, wherein said at least one spatulate member comprises a plurality of spatulate members, each extending across the width of the opening.

21. A tongue cleaning device as set forth in claim 18, wherein said scraping member further includes a brush that extends across the opening.

22. A tongue cleaning device as set forth in claim 21, wherein said brush extends transversely to said spatulate member.

23. A tongue cleaning device as set forth in claim 21, wherein said brush and said spatulate member are arranged at essentially the same level.

24. A cylindrical member for a tongue cleaning device, comprising:

a scraping member provided at a distal end of the cylindrical member for scraping a tongue surface, said scraping member including at least one spatulate member that extends across an opening of said cylindrical member, and being tilted relative to the opening so that one longitudinal edge of said spatulate member is disposed closer to a rear edge of the opening than another longitudinal edge of said spatulate member, whereby debris on the tongue surface being scraped with the scraping member is sucked through the cylindrical member by a suction system.

25. A tongue cleaning device as set forth in claim 24, wherein the scraping member includes a brush or brushy projections.

26. A tongue cleaning device as set forth in claim 24, wherein the scraping member is disposed transversely of the opening of the cylindrical member.

27. A tongue cleaning device as set forth in claim 24, wherein said cylindrical member extends in a longitudinal direction; and wherein the opening is arranged at an angle relative to the longitudinal direction, so that the opening has a length and a width, with the length being greater than the width.

28. A tongue cleaning device as set forth in claim 27, wherein said at least one spatulate member extends across the width of the opening.

29. A tongue cleaning device as set forth in claim 28, wherein said at least one spatulate member comprises a plurality of spatulate members, each extending across the width of the opening.

30. A tongue cleaning device as set forth in claim 27, wherein said scraping member further includes a brush that extends across the opening.

31. A tongue cleaning device as set forth in claim 30, wherein said brush extends transversely to said spatulate member.

32. A tongue cleaning device as set forth in claim 30, wherein said brush and said spatulate member are arranged at essentially the same level.

33. A cylindrical member for a tongue cleaning device, comprising:

a scraping member provided at a distal end of the cylindrical member for scraping a tongue surface, wherein an end of the cylindrical member is provided with a plurality of openings, each of which communicates with an interior of the cylindrical member, and wherein said scraping member comprises one of a brush and brushy projections interspersed amongst the plurality of openings, whereby debris on the tongue surface being scraped with the scraping member is sucked through the cylindrical member via the plurality of openings using a suction system.

\* \* \* \* \*